United States Patent
Tian et al.

(10) Patent No.: US 12,174,157 B2
(45) Date of Patent: *Dec. 24, 2024

(54) PROTEOMICS REACTOR, PROTEIN CHROMATOGRAPHIC SEPARATION PLATFORM AND USE THEREOF

(71) Applicant: ShenZhen BayOmics Biotechnology Co., Ltd., Guangdong (CN)

(72) Inventors: Ruijun Tian, Guangdong (CN); Wendong Chen, Guangdong (CN)

(73) Assignee: ShenZhen BayOmics Biotechnology Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/596,638

(22) Filed: Mar. 6, 2024

(65) Prior Publication Data

US 2024/0210362 A1 Jun. 27, 2024

Related U.S. Application Data

(63) Continuation of application No. 16/089,503, filed as application No. PCT/CN2017/070336 on Jan. 5, 2017, now Pat. No. 11,959,891.

(30) Foreign Application Priority Data

Mar. 31, 2016 (CN) .......................... 201610199973.1
Nov. 18, 2016 (CN) .......................... 201611031384.9

(51) Int. Cl.
*G01N 30/06* (2006.01)
*C07K 1/36* (2006.01)
*G01N 30/60* (2006.01)
*G01N 30/89* (2006.01)
*G01N 33/68* (2006.01)

(52) U.S. Cl.
CPC .............. *G01N 30/06* (2013.01); *C07K 1/36* (2013.01); *G01N 30/6078* (2013.01); *G01N 30/89* (2013.01); *G01N 33/6842* (2013.01); *G01N 2030/065* (2013.01)

(58) Field of Classification Search
None
See application file for complete search history.

(56) References Cited

U.S. PATENT DOCUMENTS 11,549,922 B2 * 1/2023 Ow .................... G01N 21/6428
11,959,891 B2 * 4/2024 Tian .................... G01N 33/6842

* cited by examiner

*Primary Examiner* — Hope A Robinson
(74) *Attorney, Agent, or Firm* — Yi Zhang; Jun He Law Offices P.C

(57) ABSTRACT

Disclosed is a proteomic reactor, comprising a pipette tip, an ion exchange resin filler and a solid-phase extraction membrane. The solid-phase extraction membrane is filled into the lower end of the pipette tip, and the ion exchange resin is filled into the lower end of the pipette tip and is located above the solid-phase extraction membrane. The ion exchange resin is a strong cation exchange resin or a strong anion exchange resin. Disclosed is a protein chromatographic separation platform comprising the proteomic reactor and a liquid chromatography-mass spectrometer. Disclosed is the use of the proteomic reactor and protein chromatographic separation platform in the protein identification and protein quantitative analysis of a cell, a tissue or a blood sample.

10 Claims, 9 Drawing Sheets

PROTEOMICS REACTOR, PROTEIN CHROMATOGRAPHIC SEPARATION PLATFORM AND USE THEREOF

CROSS-REFERENCE TO RELATED APPLICATIONS

This application is a continuation of U.S. patent application Ser. No. 16/089,503, which is the United States National Phase Application of PCT Application No. PCT/CN2017/070336 filed on Jan. 5, 2017, which claims priority to Chinese patent application No. 201610199973.1, filed on Mar. 31, 2016, and Chinese patent application No. 201611031384.9, filed on Nov. 18, 2016, the entire disclosure of each of which is incorporated herein by reference.

TECHNICAL FIELD

The present invention relates to the technical field of qualitative and quantitative proteomics, in particular to a proteomics sample preparation device, a protein chromatographic separation platform and application thereof. The fully integrated proteomics sample preparation device is termed as SISPROT (a simple, integrated and smart proteomics sample preparation technology).

BACKGROUND

In the proteomics research, protein samples are usually digested into peptides for liquid chromatography-mass spectrometry analysis to obtain protein information. This separation and identification method is the most widely used means in proteomics research.

Sample preparation in proteomics study mainly include steps of preconcentration, reduction, alkylation and enzymatic digestion of proteins, and desalting and fractionation of peptides. Conventional methods for processing protein samples involve multiple sample transfers, which would easily cause sample contamination and loss. A proteomics reactor developed in recent years has effectively integrated the above steps, greatly improving the processing efficiency of limited amount of protein sample. A Rare Cell Proteomics Reactor (RCPR), which is based on a Strong Cation Exchange (SCX) monolithic capillary column, has realized the preconcentration, reduction, alkylation and enzymatic digestion of proteins, and the fractionation of peptides, identifying 409 and 2,281 proteins from 5,000 and 50,000 cells, respectively (Mol. Cell. Proteomics 2011, 10, M110.000679). A Centrifugal Proteomics Reactor uses a centrifuge tube and SCX fillers to complete the steps of protein preparation in a centrifuge, significantly increasing the number of identified membrane proteins (Mol. Cell. Proteomics 2011, 10, 0111.008425). An in-StageTip method for performing protein sample preparation, which occurs in a narrow enclosed space, enables the protein sample preparation in a small sealed tube, and the peptide fractionation is realized by the SCX membrane and Strong Anion Exchange (SAX) membrane located at the bottom end of the small tube, identifying more than 7,000 proteins from 20 μg of protein sample (Nat. Methods 2014, 11, 319).

However, since both the protein digestion and peptide fractionation are performed on the SCX resin of the RCPR, the fractionation effect is affected; in addition, online fractionation based on salt concentration would also affect the peptide detection efficiency by mass spectrometer. The centrifugal proteomics reactor is operated in a 1.5 mL centrifuge tube, which would cause loss of the limited amount of sample. For the in-StageTip method, when the SCX membrane is used for peptide fractionation, the high concentration salt would affect the peptide detection efficiency by mass spectrometer. When SAX is used for fractionation, salt needs to be removed additionally, resulting in sample loss. In addition, when the C18 membrane is used, the high-pH reversed-phase fractionation of peptides is not realized. Moreover, lysis buffer used therein contains no detergent, which negatively affects the solubility and extraction of hydrophobic proteins.

Therefore, how to develop a high-throughput and easy-to-use proteomics sample preparation device integrating protein sample preparation, peptide SAX fractionation, and high-pH reversed-phase fractionation has become an urgent problem to be solved.

SUMMARY OF THE PRESENT INVENTION

In view of the problems in the prior art, the present invention provides a fully integrated proteomics sample preparation device termed SISPROT. By adopting the proteomics sample preparation device and the protein chromatographic separation platform provided by the present invention, the whole process of protein sample preparation, peptide strong anion exchange fractionation, high-pH reversed-phase fractionation and low-pH liquid chromatographic separation can be realized in situ, allowing large-scale identification of proteins in a limited amount of cell or tissue sample, and improving the reproducibility and the accuracy of quantitative analysis.

The "protein sample preparation" as described in the present invention refers to operations including the preconcentration, reduction, alkylation and enzymatic digestion of proteins, and the desalting and elution of peptides. Proteases, reducing agents, alkylating agents and buffer salt solutions, etc. used in various operations are all well known in the art. As typical but non-limiting examples, the proteins may be proteins extracted from tissues, cells or body fluids of biological samples or a standard protein sample; the protease may be selected from alkaline proteases such as trypsin, chymotrypsin or elastase; the reducing agent may be selected from the group consisting of dithiothreitol, trichloroethyl phosphate, β-mercaptoethanol, etc., and the alkylating agent may be iodoacetic acid or iodoacetamide, etc.

The "strong anion exchange fractionation" as described in the present invention refers to peptide fractionation based on the principle of ion exchange chromatography, which means that peptides are eluted sequentially from the strong anion exchange resins by using solutions with different pH values in an order from high to low pH to complete a strong anion exchange fractionation. The elution in an order from high to low pH when using strong anion exchange resin is compatible for the subsequent high-pH reversed-phase peptide fractionation, i.e., a high-pH reversed-phase fractionation can be performed after each strong anion exchange fraction. However, strong cation exchange resin does not have this effect, since in the strong cation exchange fractionation, elution is performed in an order from low to high pH. If a high-pH reversed-phase peptide fractionation is performed after a low-pH strong cation exchange fraction, peptides on the strong cation exchange resin will be also eluted off, and thereby the subsequent strong cation exchange fractionation (the high-pH fractionation) can no longer be performed. Therefore, the strong anion exchange fractionation and high-pH reversed-phase fractionation of peptides can be simultaneously performed when a strong anion exchange resin is used.

The terms "high-pH reversed-phase fractionation" and "low-pH liquid chromatographic separation" as described in the present invention refer to the peptide fractionation and separation based on the principle of reversed-phase liquid chromatography. The reversed-phase liquid chromatography (RPLC) is characterized in that the polarity of the stationary phase is weaker than that of the mobile phase. Due to the hydrophobicity of the RPLC stationary phase carrier, it may interact with material molecules to be separated in the mobile phase at different intensities depending on different hydrophobicity of the molecules. Therefore, different molecules can be separated from each other in the reversed-phase column. Since the interaction between the weakly hydrophobic sample molecules and the stationary phase is weaker, such molecules will be eluted out when the organic solvent content in the mobile phase is lower; on the contrary, since the interaction between the relatively more hydrophobic molecules and the stationary phase is stronger, such molecules will be eluted out when the organic solvent content in the mobile phase is higher, realizing the fractionation and separation of the peptides. In the above terms, the high-pH means a pH value above 8, such as a pH of 8, 9, 9.5 or 10; and the low-pH means a pH value below 3, such as a pH of 3, 2.5, 2, 1.5 or 1.

In order to achieve the object of the present invention, the present invention adopts the following technical solutions:

In a first aspect, the present invention provides a proteomics sample preparation device comprising a pipette tip 1, strong cation exchange resin fillers 2 and a solid-phase extraction membrane 3; wherein the solid-phase extraction membrane 3 is filled at the bottom end of the pipette tip 1, and the strong cation exchange resin fillers 2 are filled at the bottom end of the pipette tip 1 and located above the solid-phase extraction membrane 3.

In the proteomics sample preparation device as described in the first aspect, the strong cation exchange resin fillers are sulfonic acid-based.

Preferably, the solid-phase extraction membrane is a C18 membrane.

The proteomics sample preparation device as described in the first aspect can be used for in situ protein sample preparation and high-pH reversed-phase fractionation of peptides, which specifically includes: the whole process of the preconcentration, reduction, alkylation and enzymatic digestion of proteins, and the desalting, elution and high-pH reversed-phase fractionation of peptides, wherein the high-pH refers to a pH value above 8, such as pH value of 8, 9, 9.2, 9.5 or 10, etc.

The proteomics sample preparation device as described in the first aspect is operated according to the following specific operations: as shown in FIG. 1(B), placing the support block 4 at the top end of the collection tube 5, placing the proteomics sample preparation device above the collection tube 5 through the support block 4, placing the collection tube 5 into the centrifuge 6, and flowing the protein solution or reagent through the proteomics sample preparation device by centrifugation to complete operations including preconcentration and enzymatic digestion of proteins, and elution and high-pH reversed-phase fractionation of peptides, etc. In addition, the proteomics sample preparation device provided by the present invention allows automated operations; for example, the proteomics sample preparation device technology allows automated, simultaneous, and high-throughput processing of multiple samples on the automated liquid processing platform Bravo from Agilent, Inc.

In a second aspect, the present invention further provide a proteomics sample preparation device capable of integrating preparation of protein sample and strong anion exchange fractionation and high-pH reversed-phase fractionation of peptides; wherein the proteomics sample preparation device comprises a pipette tip 1, a strong anion exchange resin 2' and a solid-phase extraction membrane 3; wherein the solid-phase extraction membrane 3 is filled at the bottom end of the pipette tip 1, and the strong anion exchange resin 2' is filled at the bottom end of the pipette tip 1 and located above the solid-phase extraction membrane 3; preferably, the strong anion exchange resin 2' is quaternary ammonium group-containing resin; preferably, the solid-phase extraction membrane is a C18 membrane.

In a third aspect, the present invention provides an automated system for protein sample preparation, comprising the proteomics sample preparation device as described in the first aspect or the second aspect.

Preferably, the automated system further comprises a device capable of realizing automation, which may be a device realizing the automation by pneumatic thrust, or a device realizing the automation by vacuum pumping, and may specifically be an automated liquid processing platform and/or a peristaltic pump, for example, Agilent Bravo platform.

In a fourth aspect, the present invention provides a protein chromatographic separation platform comprising a proteomics sample preparation device I as described in the first aspect or the second aspect and a liquid chromatography-mass spectrometer II.

In a fifth aspect, the present invention further provide use of the proteomics sample preparation device as described in the first aspect or the second aspect or the protein chromatographic separation platform as described in the fourth aspect in qualitative and quantitative proteomics analysis of a cell, tissue or blood sample, especially use thereof in the large-scale qualitative and quantitative proteomics analysis of a limited amount of cell or tissue sample.

In the present invention, in a specific application of the proteomics sample preparation device as described in the first aspect, the proteomics sample preparation device is mainly used for preparation of protein sample from a biological sample and high-pH reversed-phase fractionation of peptides, wherein the protein sample from the biological sample is enzymatically digested on the strong cation or anion exchange resin fillers, and after the digestion, the resulting peptides are transferred onto the solid-phase extraction membrane, and then subjected to the high-pH reversed-phase fractionation to realize technical requirements for improving enzymatic digestion and fractionation efficiency. Preferably, the pH value of the high-pH reversed-phase fractionation is above 8.

In the present invention, when the proteomics sample preparation device as described in the first aspect is used in qualitative and quantitative proteomics analysis of a cell or tissue sample, the following specific operations are included:

(1) lysing the cell or tissue sample with a lysis buffer and acidizing the lysate, followed by adding the acidized lysate to a pre-activated proteomics sample preparation device where proteins are enriched onto the strong cation or anion exchange resin fillers by centrifugation;

(2) washing off the detergent bound to the solid-phase extraction membrane with an organic solvent-containing solution or a pure organic solvent, and adding the corresponding reagents and enzymes successively to complete the reduction, alkylation and enzymatic digestion of proteins;

(3) transferring the resulting peptides from the strong cation or anion exchange resin fillers onto the solid-phase extraction membrane by using a salt solution;

(4) desalting, followed by eluting the peptides successively by using high-pH solutions containing different proportions of organic solvent in an order from low to high proportion to perform the high-pH reversed-phase fractionation.

Preferably, the pH value of the solutions used in the fractionation in step (4) should be above 8.

The lysis buffer in step (1) comprises a detergent which is compatible for high-pH reversed-phase fractionation and liquid chromatography-mass spectrometry, and preferably is any one selected from the group consisting of n-dodecyl β-D-maltoside (DDM), cholesteryl hemisuccinate tris salt (CHS), or a mixture of two thereof.

The organic solvent-containing solution in step (2) is selected from a potassium citrate aqueous solution containing acetonitrile and/or methanol, wherein the volume content of acetonitrile and/or methanol in the solution is 20%, and the concentration of potassium citrate in the solution is 8 mmol/L.

Preferably, the pure organic solvent in step (2) is acetonitrile and/or methanol.

Preferably, the salt solution in step (3) is a volatile salt solution, preferably ammonium formate and/or ammonium bicarbonate.

In the present invention, in a specific application of the protein chromatographic separation platform as described in the fourth aspect, which comprises the proteomics sample preparation device as described in the second aspect, the protein chromatographic separation platform is mainly used for preparation of proteins in a biological sample, strong anion exchange fractionation, high-pH reversed-phase fractionation, and low-pH liquid chromatographic separation of peptides; specifically, the protein sample in the biological sample is subjected to an enzymatic digestion and a strong anion exchange fractionation on the strong anion exchange resin, and then transferred onto the solid-phase extraction membrane to perform a high-pH reversed-phase fractionation, and finally, the resulting peptides are transferred to the liquid chromatography-mass spectrometer to perform a low-pH liquid chromatographic separation and detection to realize the protein sample preparation and the three-dimensional orthogonal separation.

Preferably, the pH value of the high-pH reversed-phase fractionation is above 8.

Preferably, the pH value of the low-pH liquid chromatographic separation is below 3.

In the present invention, the protein chromatographic separation platform as described in the fourth aspect of the present invention, which comprises the proteomics sample preparation device as described in the second aspect, has the following three different operation modes, each of which can be carried out individually:

one-dimensional separation mode: i.e., the enzymatically digested protein sample is directly subjected to a low-pH liquid chromatographic separation and detection on the liquid chromatography-mass spectrometer without fractionation;

two-dimensional separation mode: i.e., the enzymatically digested protein sample is subjected to either a strong anion exchange fractionation or a high-pH reversed-phase fractionation, and then subjected to a low-pH liquid chromatographic separation and detection on the liquid chromatography-mass spectrometer;

three-dimensional separation mode: i.e., the enzymatically digested protein sample is subjected to both a strong anion exchange fractionation and a high-pH reversed-phase fractionation, and then finally subjected to a low-pH liquid chromatographic separation and detection on the liquid chromatography-mass spectrometer.

In the present invention, when the protein chromatographic separation platform as described in the fourth aspect of the present invention, which comprises the proteomics sample preparation device as described in the second aspect, is used in qualitative and quantitative proteomics analysis of a cell or tissue sample, the following specific operations are included:

(1)' lysing the cell or tissue sample with a lysis buffer and alkalizing the lysate, followed by adding the alkalized lysate to a pre-activated proteomics sample preparation device where proteins are enriched onto the strong anion exchange resin by centrifugation;

(2)' washing off the detergent bound to the solid-phase extraction membrane with an organic solvent-containing solution or a pure organic solvent, and adding the corresponding reagents and enzymes successively to complete the reduction, alkylation and enzymatic digestion of proteins;

(3)' transferring the resulting peptides from the strong anion exchange resin onto the solid-phase extraction membrane successively by using solutions with different pH values in an order from high to low pH to perform the strong anion exchange fractionation;

(4)' desalting, followed by eluting the peptides successively by using high-pH solutions containing different proportions of organic solvent in an order from low to high proportion to perform the high-pH reversed-phase fractionation;

(5)' subjecting the peptide sample to a low-pH liquid chromatographic separation and detection by using a liquid chromatography-mass spectrometer.

Preferably, the solutions with different pH values in step (3)' are used in an order from pH 12 to pH 2.

Preferably, the pH value of the solution used in the high-pH reversed-phase fractionation in step (4)' is above 8.

Preferably, the pH value of the low-pH liquid chromatographic separation in step (5)' is below 3.

The lysis buffer in step (1)' comprises a detergent which is compatible for high-pH reversed-phase fractionation and liquid chromatography-mass spectrometry, and preferably is any one selected from the group consisting of n-dodecyl β-D-maltoside (DDM), cholesteryl hemisuccinate tris salt (CHS), or a mixture of two thereof.

The organic solvent-containing solution in step (2)' is selected from a potassium citrate aqueous solution containing acetonitrile and/or methanol, wherein the volume content of acetonitrile and/or methanol in the solution is 20%, and the concentration of potassium citrate in the solution is 8 mmol/L.

Preferably, the pure organic solvent in step (2)' is acetonitrile and/or methanol.

Compared with technical solutions in the prior art, the present invention has at least the following beneficial effects:

(1) The proteomics sample preparation device as described in the first aspect of the present invention integrates operations including the preconcentration, reduction, alkylation and enzymatic digestion of proteins, and the desalting, elution and high-pH reversed-phase fractionation of peptides, etc., into one pipette tip, allowing a large-scale identification of proteins in a limited amount of cell sample, improving the reproducibility and the accuracy of quantitative analysis, and realizing efficient digestion of proteins within 15 min.

(2) The proteomics sample preparation device as described in the second aspect of the present invention integrates operations including preparation of protein sample and strong anion exchange fractionation and high-pH reversed-phase fractionation of peptides, etc., into one pipette tip, allowing a large-scale identification of proteins in a limited amount of cell sample, and improving the reproducibility and the accuracy of quantitative analysis.

(3) The present invention also relates to a compatible lysis buffer, i.e., the lysis buffer comprises a detergent which is compatible for high-pH reversed-phase fractionation and liquid chromatography-mass spectrometry, such as n-dodecyl-β-D-maltoside and Cholesteryl hemisuccinate tris salt (CHS), so that the high-pH reversed-phase fractionation of peptide can be integrated into the proteomics sample preparation device of the present invention, improving the number of identified proteins.

(4) The present invention also relates to an operation for cleaning the detergent on the C18 membrane, i.e., after enriching proteins onto the strong cation/anion exchange resin fillers, washing off the detergent bound to the C18 membrane by using an organic solvent-containing solution or a pure organic solvent.

(5) The proteomics sample preparation device as described in the first aspect of the present invention performs enzymatic digestion of proteins and fractionation of peptides on different materials, i.e., proteins are enzymatically digested on the strong cation or anion exchange resin fillers, and after the digestion, the resulting peptides are transferred onto the C18 membrane, followed by the high-pH reversed-phase fractionation, which is conducive to improving the efficiency of the digestion and the fractionation.

(6) The protein chromatographic separation platform as described in the fourth aspect of the present invention, which comprises the proteomics sample preparation device as described in the second aspect, integrates operations including the preconcentration, reduction, alkylation and enzymatic digestion of proteins, and strong anion exchange fractionation and high-pH reversed-phase fractionation of peptides, etc., into one pipette tip, and when combining with the low-pH chromatographic separation by the liquid chromatography-mass spectrometer, can achieve a three-dimensional separation and a large-scale identification of proteins in a limited amount of cell, tissue or blood sample, improving the reproducibility and the accuracy of quantitative analysis;

(7) The proteomics sample preparation device encompassed by the present invention allows an automated operation; for example, the proteomics sample preparation device technology allows automated, simultaneous and high-throughput processing of multiple samples on the automated liquid processing platform Bravo from Agilent Inc.

Wherein: 1—pipette tip, 2—strong cation exchange resin fillers, 3—C18 membrane, 4—support block, 5—collection tube, 6—centrifuge.

Figure 2:
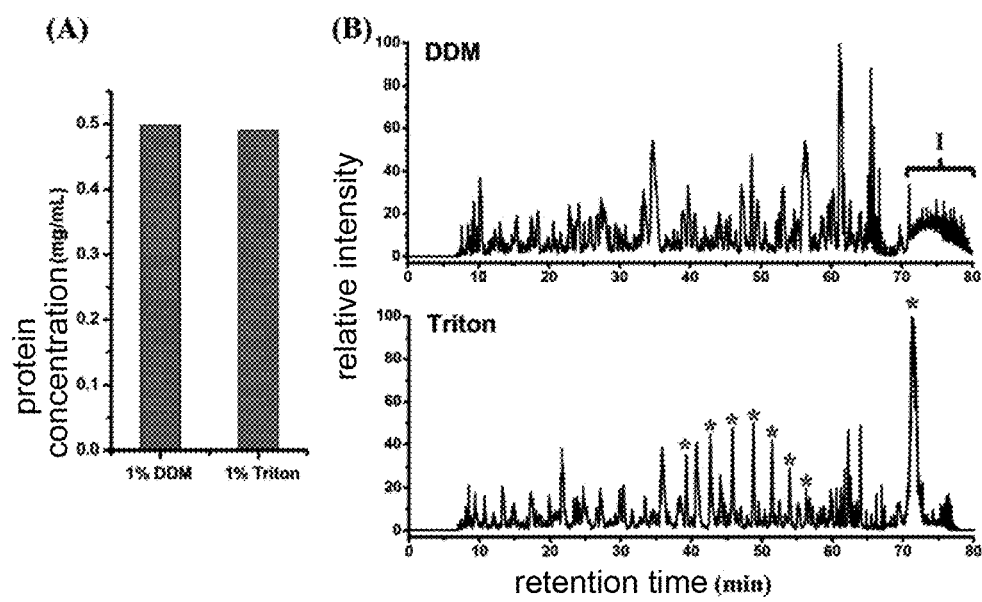

FIG. 2 shows (A) a comparison of protein extraction efficiency of the lysis buffer; (B) a comparison of the peptide chromatograms, in which the peak containing DDM is marked with "I" and the peak containing octylphenol polyethoxyethanol (OPE) is marked with "*", when the detergent is 1% (w/v) DDM or 1% (v/v) octylphenol polyethoxyethanol (OPE).

Figure 3:
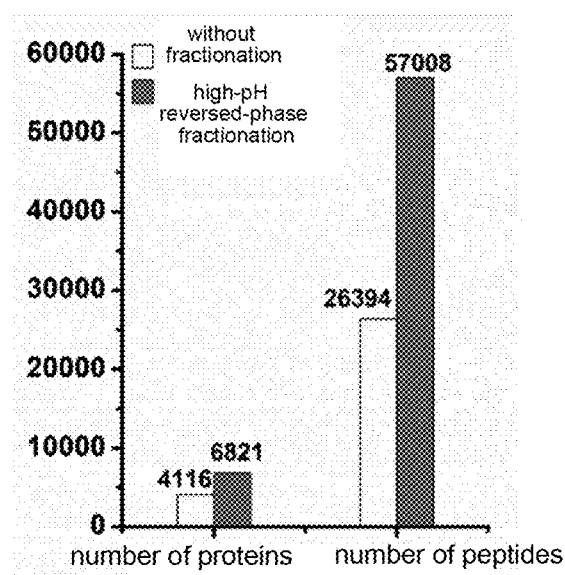

FIG. 3 shows comparisons of the numbers of proteins and peptides as identified upon the high-pH reversed-phase fractionation of the present invention and without fractionation.

Figure 4:
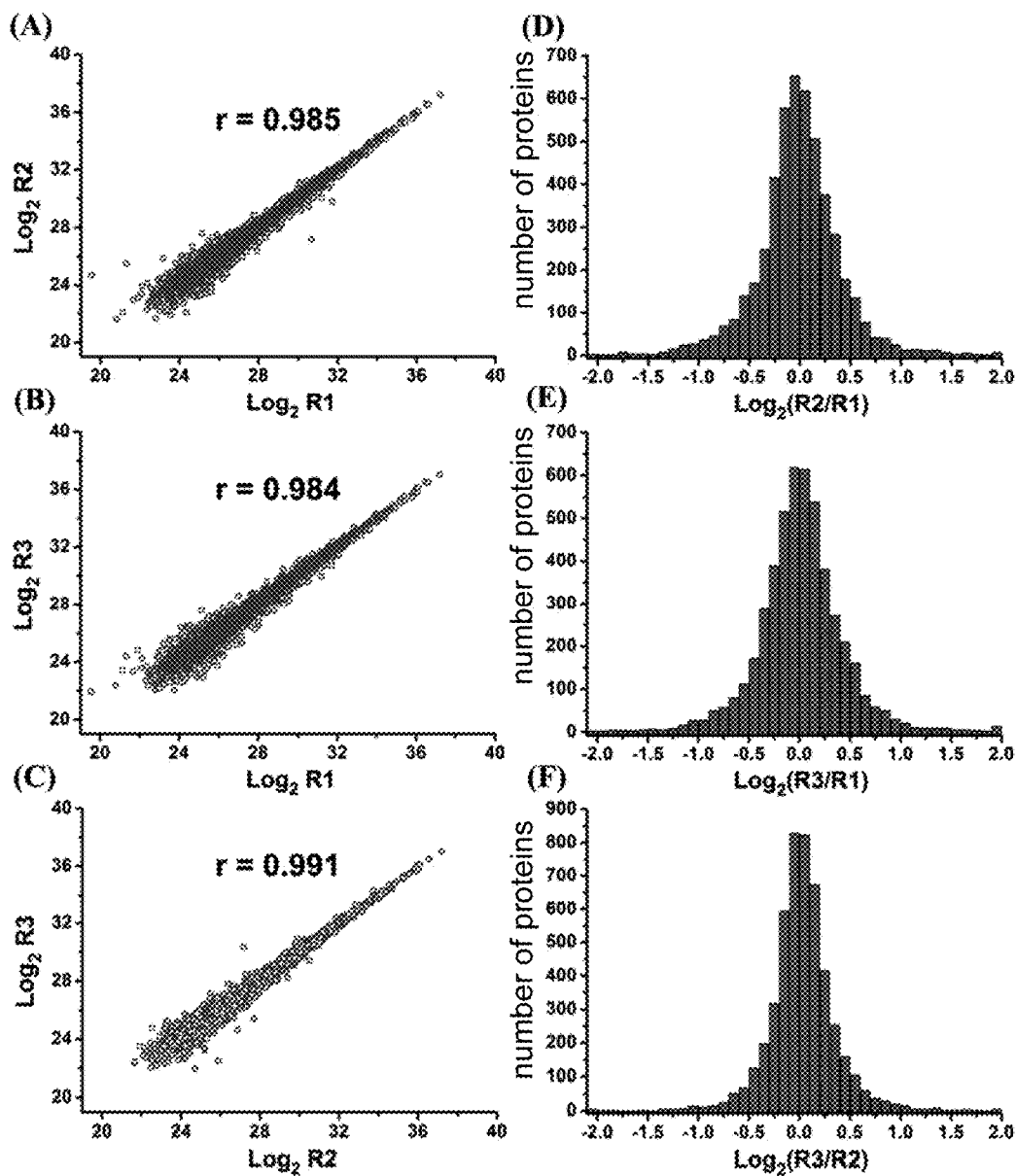

FIG. 4 shows a performance evaluation on the label-free quantitative analysis of the proteomics sample preparation device as described in the first aspect of the present invention. Wherein, (A)-(C) are the linear fitting results of the label-free quantitative intensities of the proteins identified in any two experiments; and (D)-(F) are the distributions of the label-free quantitative intensity ratios of the proteins identified in any two experiments. R1, R2 and R3 represent the label-free quantitative intensities of the proteins identified in experiments 1, 2 and 3, respectively.

Figure 5:
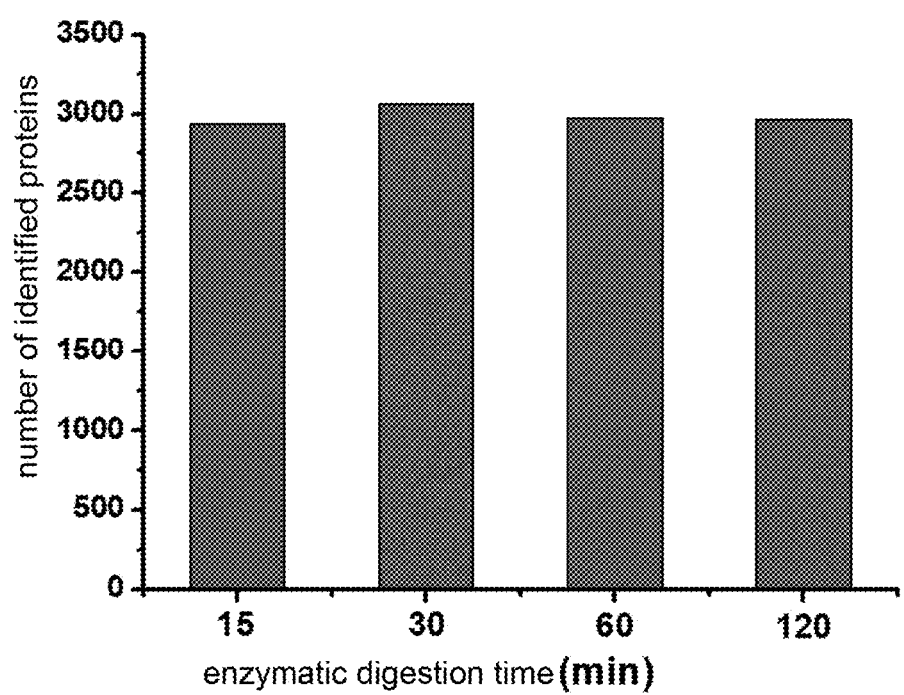

FIG. 5 shows the effect of enzymatic digestion time on the number of the identified proteins.

Figure 6A:
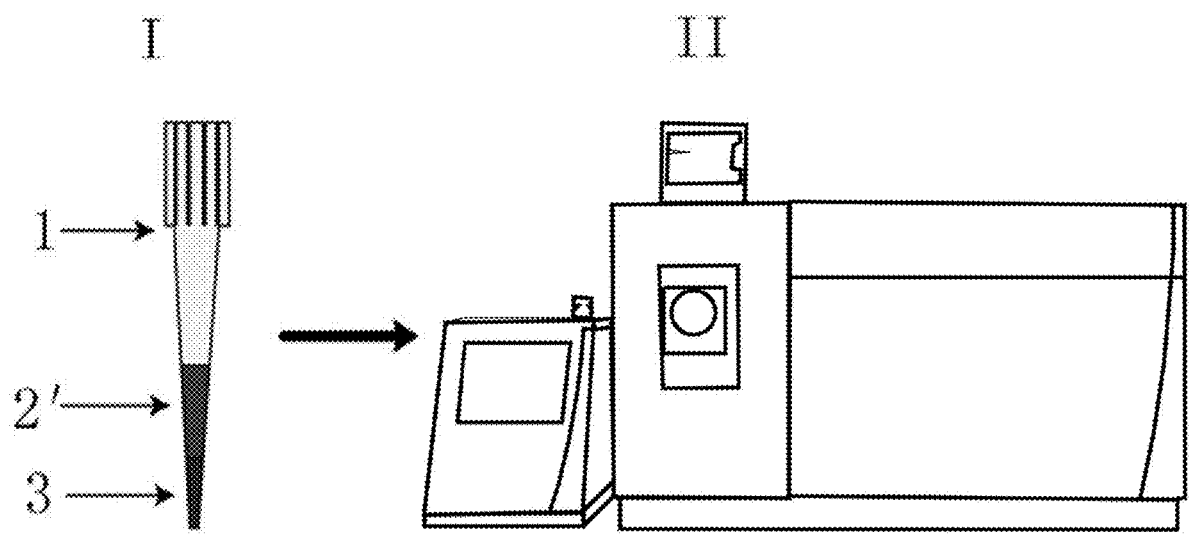
Figure 6B:
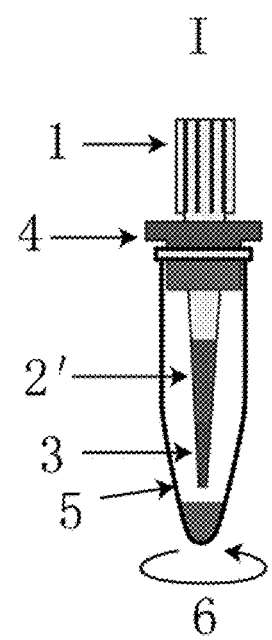

FIG. 6 shows the protein chromatographic separation platform as described in the fourth aspect of the present invention, which comprises the proteomics sample preparation device as described in the second aspect, wherein FIG. 6(A) is a protein chromatographic separation platform, and FIG. 6(B) is the structure diagram when it is specifically operated, in which: 1—pipette tip, 2—strong anion exchange resin, 3—C18 membrane, 4—support block, 5—collection tube, 6—centrifuge.

Figure 7A:
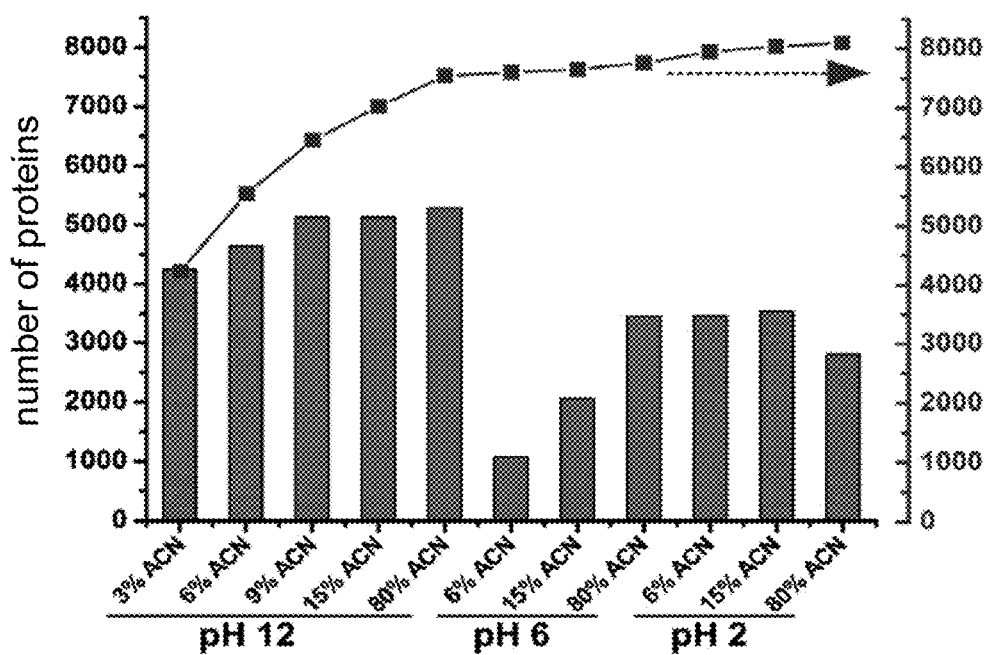
Figure 7B:
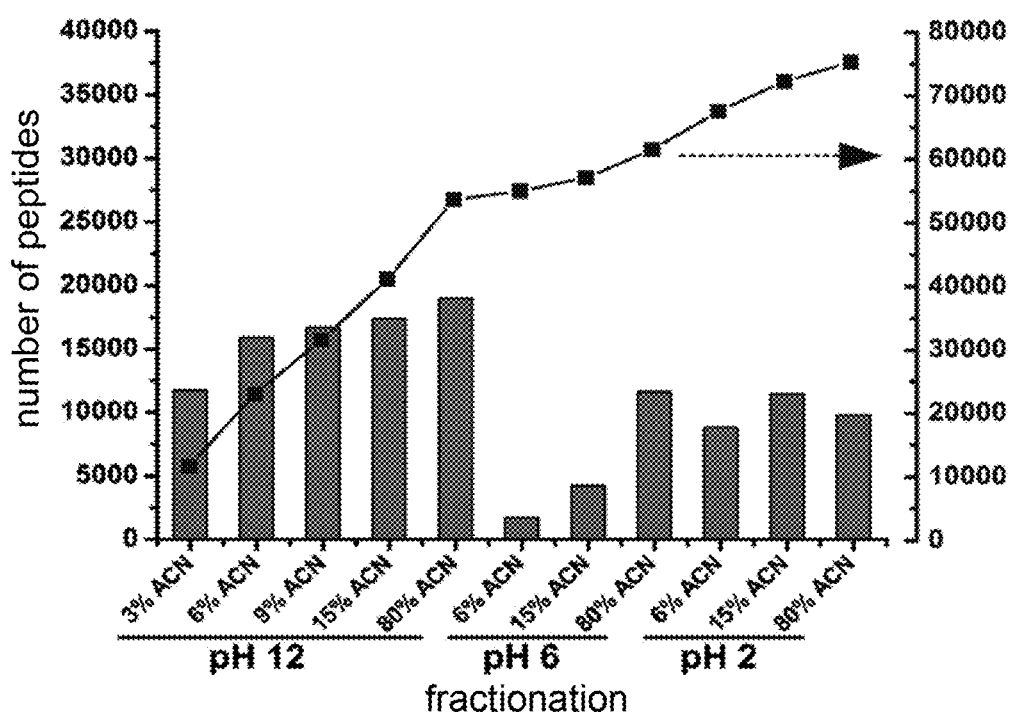

FIG. 7 is a diagram showing the distribution of the numbers of proteins and peptides identified in each fraction when 30 μg of cell lysates were analyzed by using the protein chromatographic separation platform as described in the fourth aspect of the present invention, which comprises the proteomics sample preparation device as described in the second aspect, wherein, FIG. 7(A) shows the distribution of the number of proteins and the cumulative change of the number of proteins with the fractionation, and FIG. 7(B) shows the distribution of the number of peptides and the cumulative change of the number of peptides with the fractionation.

The present invention is further described in detail below. However, the following examples are merely illustrative examples of the present invention, but do not represent or limit the protection scope of the present invention. The protection scope of the present invention is defined by the claims.

DETAILED DESCRIPTION

In order to further illustrate the present invention and facilitate to understand the technical solutions of the present invention, typical but non-limiting examples of the present invention are as follows:

In the examples, techniques or conditions, which are not specifically indicated, are performed according to techniques or conditions described in the literature of the art, or according to product instructions. The reagents or instruments for use, which are not indicated with manufacturers, are conventional products that are commercially available from formal sources.

First, a compatible lysis buffer is provided by the present invention. Lysis buffer used in the rare cell proteomics reactor (RCPR) has a composition of 10 mmol/L HEPES, pH 7.4, 150 mmol/L NaCl, 2 mmol/L CaCl2, 2 mmol/L MgCl2, 600 mmol/L guanidine hydrochloride, 1% octylphenol polyethoxyethanol (OPE) and protease inhibitors, and is very suitable for the lysis of a limited amount of cells. However, the detergent, octylphenol polyethoxyethanol (OPE), in the lysis buffer is not compatible with liquid chromatography-mass spectrometry. As shown in FIG. 2(B), when using this lysis buffer, many strong peaks associated with octylphenol polyethoxyethanol (OPE) were present in the peptide chromatogram, affecting the detection of peptides. Therefore, we replaced 1% octylphenol polyethoxyethanol (OPE) by 1% DDM. As shown in FIG. 2(A), the 1% DDM-containing lysis buffer had comparable protein extraction efficiency to that of the original RCPR lysis buffer. Moreover, it was shown in the peptide chromatogram (FIG. 2(B)) that peaks associated with DDM did not appear until the final time period, which would not affect the detection of peptides. Therefore, the DDM-containing lysis buffer of the present invention is compatible for liquid chromatography-mass spectrometry.

The proteomics sample preparation device as described in the first aspect of the present invention integrates the high-pH reversed-phase fractionation of peptides, increasing the numbers of identified peptides and proteins. As shown in FIG. 3, when 50,000 HEK 293T cells were analyzed, 57,008 peptides and 6,821 proteins were identified upon the high-pH reversed-phase fractionation, which were 2.2-fold and 1.7-fold, respectively, as high as those without fractionation.

The proteomics sample preparation device of the present invention as described in the first aspect has a higher sensitivity. As shown in Table 1, 6 μg of protein sample from HEK 293T cells was processed equally without fractionation. 19,493 peptides and 3,693 proteins were identified by the proteomics sample preparation device as described in the first aspect of the present invention, respectively, which were 2.8-fold and 1.7-fold as high as those by using the centrifugal proteomics sample preparation device, respectively.

As shown in Table 2, 1,270, 2,566, 5,749, 6,821, and 7,826 proteins were identified respectively from 2,000, 5,000, 20,000, 50,000, and 100,000 HEK 293T cells by using the proteomics sample preparation device as described in the first aspect of the present invention. In contrast, 409 and 2,281 proteins were identified respectively from 5,000 and 50,000 cells by using RCPR. In the case of the same amount of cells, the sensitivity of the proteomics sample preparation device as described in the first aspect of the present invention was 6.3-fold and 3.0-fold as high as that by using the RCPR.

TABLE 1

| Technology | Number of identified peptides | Number of identified proteins |
| --- | --- | --- |
| Proteomic reactor as described in the first aspect of the invention | 19,493 | 3,693 |
| Centrifugal proteomic reactor | 6,888 | 2,145 |

TABLE 2

| Number of cells | Number of identified peptides | Number of identified proteins | number of fractionations |
| --- | --- | --- | --- |
| 2,000 | 4,359 | 1,270 | no |
| 5,000 | 11,820 | 2,566 | no |
| 20,000 | 41,115 | 5,749 | 5 |
| 50,000 | 57,008 | 6,821 | 5 |
| 100,000 | 87,773 | 7,826 | 5 |

The proteomics sample preparation device as described in the first aspect of the present invention was applied to a sample of 100,000 stem cells from human exfoliated deciduous teeth (SHED). The results from three experiments were shown in Table 3. More than 7,000 proteins were identified in each experiment, and a total of 120,456 peptides and 9,078 proteins were identified in the three experiments, representing the largest protein data set for SHED cells to date.

TABLE 3

| Experiment No. | Number of identified peptides | Number of identified proteins |
| --- | --- | --- |
| Experiment 1 | 87,150 | 7,765 |
| Experiment 2 | 78,211 | 7,257 |
| Experiment 3 | 77,650 | 7,364 |
| Combined result | 120,456 | 9,078 |

The MaxQuant software was used to obtain the label-free quantitative intensity of the proteins identified in the three experiments. The linear fitting results of any two experiments were shown in FIG. 4, with a Pearson correlation coefficient r greater than 0.98. The distributions of the label-free quantitative intensity ratios of the proteins identified in any two experiments were shown in FIG. 4, in which 97% of protein has a ratio change less than 2. The results indicated that the sensitivity and label-free quantitative analysis capability of the proteomics sample preparation device of the present invention as described in the first aspect are comparable to those of the in-StageTip method for protein sample preparation.

Since the conventional in-solution digestion protocol requires overnight digestion, the proteomics sample preparation device as described in the first aspect of the present invention has the advantages of shorter digestion time and higher digestion efficiency. As shown in FIG. 5, more than 2,900 proteins were identified when 20,000 HEK 293T cells were treated with the proteomics sample preparation device without fractionation. In addition, the number of identified proteins was not reduced when the digestion time was reduced from 120 minutes to 15 minutes. Therefore, proteins can be efficiently enzymatically digested within 15 minutes by using the proteomics sample preparation device as described in the first aspect of the present invention.

Example 1

Figure 1:
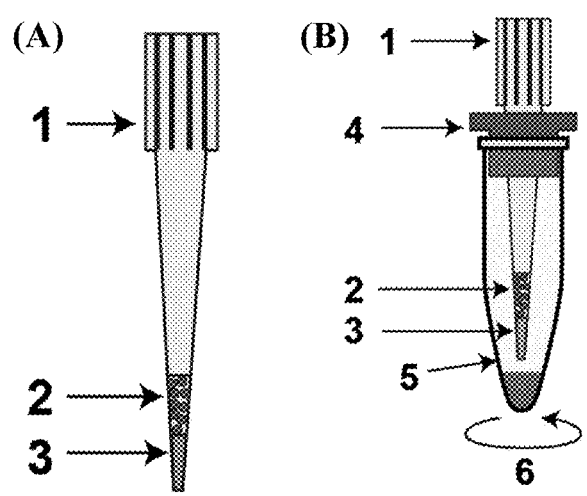
FIG. 1 shows the structure diagram of the proteomics sample preparation device as described in the first aspect of the present invention (A) as well as that when it is specifically operated (B).

As shown in FIGS. 1(A) and (B), a proteomics sample preparation device integrating protein preparation and high-pH reversed-phase fractionation of peptide comprised a pipette tip 1, strong cation exchange resin fillers 2, and a C18 membrane 3. Wherein, the pipette tip 1 was a standard 200 μL pipette tip, the C18 membrane 3 (3M Empore, USA) was filled at the bottom end of the pipette tip 1, with a length of about 3 mm, and 1.2 mg of strong cation exchange resin fillers (sulfonic acid-based strong cation exchange resin fillers) 2 (Applied Biosystems, USA) were filled at the bottom end of the pipette tip 1 and located above the C18 membrane 3.

The support block 4 was placed at the top end of the 1.5 mL collection tube 5. The proteomics sample preparation device was placed above the collection tube 5 through the support block 4. The collection tube 5 was placed into the centrifuge 6. The protein sample or reagent was flowed through the proteomics sample preparation device by centrifugation to complete operations including preconcentration and enzymatic digestion of proteins, and desalting and high-pH reversed-phase fractionation of peptides, which had the following specific steps:

To a sample of 50,000 cells, 25 µL of compatible lysis buffer consisting of 10 mmol/L HEPES, pH 7.4, 150 mmol/L NaCl, 2 mmol/L CaCl2, 2 mmol/L MgCl2, 600 mmol/L guanidine hydrochloride, 1% DDM and protease inhibitors was added. Upon lysis, the sample solution was acidified to pH 2 by the addition of trifluoroacetic acid. The proteomics sample preparation device was firstly activated by 20 µL of methanol, 20 µL of 100 mmol/L potassium citrate aqueous solution and 20 µL of 10 mmol/L potassium citrate aqueous solution, respectively. After the activation, the sample was added into the proteomics sample preparation device, and proteins were concentrated onto the strong cation exchange resin fillers 2 by centrifugation in the centrifuge 6; then, the detergent DDM bound to C18 membrane 3 was washed off with an 8 mmol/L potassium citrate aqueous solution containing 20% acetonitrile; then, 10 mmol/L Tris(2-carboxyethyl)phosphine hydrochloride (TCEP) solution was added to react at room temperature for 15 minutes to complete the reduction of proteins. Then, the TCEP was washed off by adding 20 µL of ultrapure water, and then 4 µg trypsin in 10 mmol/L iodoacetamide solution was added to react at room temperature in a dark environment for 60 minutes to complete alkylation and enzymatic digestion of proteins. Then, the resulting peptides were transferred from the strong cation exchange resin fillers 2 to the C18 membrane 3 by using 20 µL of 200 mmol/L ammonium formate aqueous solution; and then, 20 µL of 5 mmol/L ammonium formate aqueous solution was added for desalting. Finally, peptides were eluted off sequentially by using 5 mmol/L ammonium formate solutions respectively containing 3%, 6%, 9%, 15%, and 80% acetonitrile at a pH of 10, i.e., a high-pH reversed-phase fractionation was performed. The eluted peptides were lyophilized to dryness and re-dissolved in 0.1% formic acid aqueous solution for further analysis with a liquid chromatography-mass spectrometer.

The proteomics sample preparation device as described in the first aspect of the present invention integrates an operation of high-pH reversed-phase fractionation of peptide, thus the numbers of identified peptides and proteins were increased. As shown in FIG. 3, when 50,000 HEK 293T cells were analyzed, 57,008 peptides and 6,821 proteins were identified upon the high-pH reversed-phase fractionation, which were 2.2-fold and 1.7-fold, respectively, as high as those without fractionation.

Example 2

A proteomics sample preparation device integrating protein preparation and high-pH reversed-phase fractionation of peptide comprised a pipette tip 1, strong cation exchange resin fillers 2, and a C18 membrane 3. Wherein, the pipette tip 1 was a standard 200 µL pipette tip, the C18 membrane 3 (3M Empore, USA) was filled at the bottom end of the pipette tip 1, with a length of about 3 mm, and 1.2 mg of strong cation exchange resin fillers (sulfonic acid-based strong cation exchange resin fillers) 2 (Applied Biosystems, USA) were filled at the bottom end of the pipette tip 1 and located above the C18 membrane 3.

The support block 4 was placed at the top end of the 1.5 mL collection tube 5. The proteomics sample preparation device was placed above the collection tube 5 through the support block 4. The collection tube 5 was placed into the centrifuge 6. The protein sample or reagent was flowed through the proteomics sample preparation device by centrifugation to complete operations including preconcentration and digestion of proteins, and desalting and high-pH reversed-phase fractionation of peptides, which had the following specific steps:

To four cell samples with 20,000 cells per sample, 25 µL of compatible lysis buffer consisting of 10 mmol/L HEPES, pH 7.4, 150 mmol/L NaCl, 2 mmol/L CaCl2, 2 mmol/L MgCl2, 600 mmol/L guanidine hydrochloride, 1% DDM and protease inhibitors was added respectively. Upon lysis, the sample solutions were acidified to pH 2 by the addition of trifluoroacetic acid. The proteomics sample preparation device was firstly activated by 20 µL of methanol, 20 µL of 100 mmol/L potassium citrate aqueous solution, and 20 µL of 10 mmol/L potassium citrate aqueous solution, respectively. After the activation, the samples were added into the proteomics sample preparation device, and proteins were concentrated onto the strong cation exchange resin fillers 2 by centrifugation in the centrifuge 6; then, the detergent DDM bound to C18 membrane 3 was washed off with an 8 mmol/L potassium citrate aqueous solution containing 20% acetonitrile; then, 10 mmol/L Tris(2-carboxyethyl)phosphine hydrochloride (TCEP) solution was added to react at room temperature for 15 minutes to complete the reduction of proteins. Then, the TCEP was washed off by adding 20 µL of ultrapure water, and then 4 µg trypsin in 10 mmol/L iodoacetamide was added to react at room temperature in a dark environment for 15, 30, 60 and 120 minutes, respectively, to complete alkylation and enzymatic digestion of proteins. Then, the resulting peptides were transferred from the strong cation exchange resin fillers 2 to the C18 membrane 3 by using 20 µL of 200 mmol/L ammonium formate aqueous solution; and then, 20 µL of 5 mmol/L ammonium formate aqueous solution was added for desalting. Finally, peptides were eluted off by using 5 mmol/L ammonium formate solution containing 80% acetonitrile with a pH of 10. The eluted peptides were lyophilized to dryness and re-dissolved in 0.1% formic acid aqueous solution for further analysis with a liquid chromatography-mass spectrometer.

As shown in FIG. 5, more than 2,900 proteins were identified when 20,000 HEK 293T cells were treated with the proteomics sample preparation device of this example without fractionation. In addition, the number of the identified proteins was not reduced when the digestion time was reduced from 120 minutes to 15 minutes. Therefore, proteins can be efficiently enzymatically digested within 15 minutes by using the proteomics sample preparation device of this example.

Example 3

As shown in FIG. 6(A), a protein chromatographic separation platform included a proteomics sample preparation device I and a liquid chromatography-mass spectrometer II (Orbitrap Fusion, Thermo Fisher Scientific, USA); wherein the proteomics sample preparation device I included a standard 200 μL pipette tip 1, a strong anion exchange membrane 2' (3M Empore, USA) and a C18 membrane 3 (3M Empore, USA); the C18 membrane 3 was filled at the bottom end of the pipette tip 1, the strong anion exchange membrane 2' was filled at the bottom end of the pipette tip 1 and located above the C18 membrane 3.

As shown in FIG. 6(B), when being in operation, the support block 4 was placed at the top end of the 1.5 mL collection tube 5. The proteomics sample preparation device was placed above the collection tube 5 through the support block 4. The collection tube 5 was placed into the centrifuge 6. The protein solution or reagent was flowed through the proteomics sample preparation device by centrifugation to complete operations including preconcentration and enzymatic digestion of proteins, and peptide desalting, which had the following specific steps:

The cell or tissue samples were lysed by using a compatible lysis buffer consisting of 25 mmol/L HEPES, pH 7.4, 150 mmol/L NaCl, 2 mmol/L CaCl2, 2 mmol/L MgCl2, 600 mmol/L guanidine hydrochloride, 1% DDM and protease inhibitors. Protein components were extracted therefrom and the protein concentrations were measured. 6 μg of protein sample was used, and the sample solution was alkalized to pH 12 by the addition of 3 mol/L aqueous ammonia. The proteomics sample preparation device was firstly activated by 20 μL of methanol and 20 μL of 3 mol/L aqueous ammonia, respectively. After the activation, the sample was added into the proteomics sample preparation device, and proteins were concentrated onto the strong anion exchange membrane 2' by centrifugation in the centrifuge 6; then, the detergent DDM bound to the C18 membrane 3 was washed off by using 3 mol/L ammonia aqueous solution containing 20% acetonitrile (ACN); and then, 50 mmol/L dithiothreitol (DTT) solution was added to react at room temperature for 30 minutes to complete the reduction of proteins. Then, 5 μL of 20 mmol/L ammonium bicarbonate was added to wash off the DTT, and then 4 μg trypsin in 10 mmol/L iodoacetamide solution was added to react at room temperature in a dark environment for 60 minutes to complete alkylation and enzymatic digestion of proteins. Then, the resulting peptides were transferred from the strong anion exchange membrane 2' to the C18 membrane 3 by using 20 μL of solution containing 250 mmol/L NaCl, pH 2; and then, 20 μL of 1% formic acid aqueous solution was added for desalting. Finally, peptides were eluted off by using 40 μL of 80% acetonitrile-0.5% acetic acid solution. The eluted peptides were lyophilized to dryness and re-dissolved in 0.1% formic acid aqueous solution for low-pH liquid chromatographic separation and detection on a liquid chromatography-mass spectrometer, i.e., in an operation mode of one-dimensional separation.

The results were shown in Table 4, which indicated that 19,949 peptides and 4,269 proteins were identified.

TABLE 4

Numbers of peptides and proteins identified in an operation mode of one-dimensional separation

| operation mode | aample amount (μg) | number of peptides | number of proteins | number of fraction-ation | mass spectrom-etry time (h) |
|---|---|---|---|---|---|
| one-dimensional separation | 6 | 19,949 | 4,269 | no | 1.4 |

Example 4

As shown in FIG. 6(A), a protein chromatographic separation platform included a proteomics sample preparation device I and a liquid chromatography-mass spectrometer II (Orbitrap Fusion, Thermo Fisher Scientific, USA); wherein the proteomics sample preparation device I included a standard 200 μL pipette tip 1, a strong anion exchange membrane 2' (3M Empore, USA) and a C18 membrane 3 (3M Empore, USA); the C18 membrane 3 was filled at the bottom end of the pipette tip 1, the strong anion exchange membrane 2' was filled at the bottom end of the pipette tip 1 and located above the C18 membrane 3.

As shown in FIG. 6(B), when being in operation, the support block 4 was placed at the top end of the 1.5 mL collection tube 5. The proteomics sample preparation device I was placed above the collection tube 5 through the support block 4. The collection tube 5 was placed into the centrifuge 6. The protein solution or reagent was flowed through the proteomics sample preparation device by centrifugation to complete operations including preconcentration and enzymatic digestion of proteins, and strong anion exchange fractionation of peptides, which had the following specific steps:

The cell or tissue samples were lysed by using a compatible lysis buffer consisting of 25 mmol/L HEPES, pH 7.4, 150 mmol/L NaCl, 2 mmol/L CaCl2, 2 mmol/L MgCl2, 600 mmol/L guanidine hydrochloride, 1% DDM and protease inhibitors. Protein components were extracted therefrom and the protein concentrations were measured. 30 μg of protein sample was used, and the sample solution was alkalized to pH 12 by the addition of 3 mol/L aqueous ammonia. The proteomics sample preparation device was firstly activated by 60 μL of methanol and 60 μL of 3 mol/L aqueous ammonia, respectively. After the activation, the sample was added into the proteomics sample preparation device, and proteins were concentrated onto the strong anion exchange membrane 2' by centrifugation in the centrifuge 6; then, the detergent DDM bound to the C18 membrane 3 was washed off by using 3 mol/L ammonia aqueous solution containing 20% ACN; and then, 50 mmol/L DTT solution was added to react at room temperature for 30 minutes to complete the reduction of proteins. Then, 5 μL of 20 mmol/L ammonium bicarbonate was added to wash off the DTT, and then 8 μg trypsin in 10 mmol/L iodoacetamide solution was added to react at room temperature and in a dark environment for 60 minutes to complete alkylation and enzymatic digestion of proteins. Then, the resulting peptides were transferred from the strong anion exchange membrane 2' to the C18 membrane 3 by using 20 μL of solution with a pH of 12, 6 and 2 respectively, i.e., a strong anion exchange fractionation was performed. The solutions used in the above fractionation consisted of 20 mmol/L CH3COOH, 20 mmol/L H3PO4 and 20 mmol/L H3BO3, and the pH was adjusted with NaOH. After each strong anion exchange fractionation, 20 μL of 5 mmol/L ammonium formate aqueous solution was added for desalting. Then, peptides were eluted off by using 5 mmol/L ammonium formate solution containing 80% acetonitrile with a pH of 10. The eluted peptides were lyophilized to dryness and re-dissolved in 0.1% formic acid aqueous solution for low-pH liquid chromatographic separation and detection on a liquid chromatography-mass spectrometer, i.e., in an operation mode of two-dimensional separation.

The results were shown in Table 5, which indicated that 35,085 peptides and 5,324 proteins were identified.

TABLE 5

Numbers of peptides and proteins identified in an operation mode of two-dimensional separation

| operation mode | sample amount (μg) | number of peptides | number of proteins | number of fractionation | mass spectrometry time (h) |
|---|---|---|---|---|---|
| two-dimensional separation | 30 | 35,085 | 5,324 | 3 | 4.2 |

Example 5

As shown in FIG. 6(A), a protein chromatographic separation platform included a proteomics sample preparation device I and a liquid chromatography-mass spectrometer II (Orbitrap Fusion, Thermo Fisher Scientific, USA); wherein the proteomics sample preparation device I included a standard 200 μL pipette tip 1, a strong anion exchange membrane 2' (3M Empore, USA) and a C18 membrane 3 (3M Empore, USA); the C18 membrane 3 was filled at the bottom end of the pipette tip 1, the strong anion exchange membrane 2' was filled at the bottom end of the pipette tip 1 and located above the C18 membrane 3.

As shown in FIG. 6(B), when being in operation, the support block 4 was placed at the top end of the 1.5 mL collection tube 5. The proteomics sample preparation device was placed above the collection tube 5 through the support block 4. The collection tube 5 was placed into the centrifuge 6. The protein solution or reagent was flowed through the proteomics sample preparation device by centrifugation to complete operations including preconcentration and enzymatic digestion of proteins, strong anion exchange fractionation and high-pH reversed-phase fractionation of peptides, which had the following specific steps:

The cell or tissue samples were lysed by using a compatible lysis buffer consisting of 25 mmol/L HEPES, pH 7.4, 150 mmol/L NaCl, 2 mmol/L CaCl2, 2 mmol/L MgCl2, 600 mmol/L guanidine hydrochloride, 1% DDM and protease inhibitors. Protein components were extracted therefrom and the protein concentrations were measured. 30 μg of protein sample was used, and the sample solution was alkalized to pH 12 by the addition of 3 mol/L aqueous ammonia. The proteomics sample preparation device was firstly activated by 60 μL of methanol and 60 μL of 3 mol/L aqueous ammonia, respectively. After the activation, the sample was added into the proteomics sample preparation device, and proteins was concentrated onto the strong anion exchange membrane 2' by centrifugation in the centrifuge 6; then, the detergent DDM bound to the C18 membrane 3 was washed off by using 3 mol/L ammonia aqueous solution containing 20% ACN; then, 50 mmol/L DTT solution was added to react at room temperature for 30 minutes to complete the reduction of proteins. Then, 5 μL of 20 mmol/L ammonium bicarbonate was added to wash off the DTT, and then 8 μg trypsin in 10 mmol/L iodoacetamide solution was added to react at room temperature and in a dark environment for 60 minutes to complete alkylation and enzymatic digestion of proteins. Then, the resulting peptides were transferred from the strong anion exchange membrane 2' to the C18 membrane 3 by using 20 μL of solution with a pH of 12, 8, 6, 5, 4 and 2 respectively, i.e., a strong anion exchange fractionation was performed. The solutions used in the above fractionation consisted of 20 mmol/L CH3COOH, 20 mmol/L H3PO4 and 20 mmol/L H3BO3, and the pH was adjusted with NaOH. After each strong anion exchange fraction, 20 μL of 5 mmol/L ammonium formate aqueous solution was added for desalting. Then, peptides were eluted off successively by using 5 mmol/L ammonium formate solutions respectively containing 3%, 6%, 9%, 15%, 80% acetonitrile with a pH of 10, i.e., a high-pH reversed-phase fractionation was performed. The eluted peptides were lyophilized to dryness and re-dissolved in 0.1% formic acid aqueous solution for low-pH liquid chromatographic separation and detection on a liquid chromatography-mass spectrometer, i.e., in an operation mode of three-dimensional separation.

The results were shown in Table 6, which indicated that 75,298 peptides and 8,097 proteins were identified.

TABLE 6

Numbers of peptides and proteins identified in an operation mode of three-dimensional separation

| operation mode | sample amount (μg) | number of peptides | number of proteins | number of fractionation | mass spectrometry time (h) |
|---|---|---|---|---|---|
| three-dimensional separation | 30 | 75,298 | 8,097 | 11 | 20.4 |

Upon the three-dimensional separation, the numbers of identified proteins and peptides were greatly increased. FIG. 7 is a diagram showing the distribution of the numbers of proteins (Figure (A)) and peptides (Figure (B)) identified in each fraction. The cumulative changes in the numbers of proteins (Figure (A)) and peptides (Figure (B)) with the fractions were given in the diagram meanwhile. It can be seen that, except 2 fractions that identified less proteins and peptides, the numbers of proteins and peptides identified in the other 9 fractions had a uniform distribution, showing a better fractionation effect.

The Applicant declares that detailed structural features of the present invention have been described through the above examples, and however, the present invention is not limited to the above detailed structural features. That is to say, it does not mean that the implementation of the present invention must rely on the above detailed structural features. Those skilled in the art should understand that any improvement on the present invention, including the equivalent replacement and the addition of auxiliary parts to the selected parts of the present invention, and the selection of specific methods, etc., falls within the protection scope and the disclosure scope of the present invention.

The preferred embodiments of the present invention have been described in detail above. However, the present invention is not limited to the specific details in the above embodiments. Various simple variations of the technical solutions of the present invention may be made within the technical concept of the present invention, and all these simple variations belong to the protection scope of the present invention.

In addition, it should be noted that the specific technical features described in the above specific embodiments can be combined in any suitable manner without contradiction. In order to avoid unnecessary duplication, various possible combinations will not be further explained in the present invention.

In addition, any combination may also be made between various different embodiments of the present invention as long as it does not violate the idea of the present invention, which should also be regarded as disclosure of the present invention.

What is claimed is:

1. A chromatographic separation device for preparing a sample for proteomics analysis, comprising: (a) a sample preparation device which comprises: (1) a pipette tip of about 200 uL; (2) a solid-phase extraction membrane with a length of about 3 mm filled at the bottom end of the pipette tip; and (3) a layer of strong cation exchange resin or strong anion exchange resin located above the solid-phase extraction membrane, wherein the sample preparation device does not comprise a second solid-phase extraction membrane located above the layer of strong cation exchange resin or strong anion exchange resin; (b) a lysis buffer for lysing a biological sample into a plurality of proteins, comprising HEPES, NaCl, guanidine hydrochloride, n-dodecyl β-D-maltoside (DDM), and a protease inhibitor; (c) a digesting reagent for digesting the plurality of proteins retained in the layer of strong cation exchange resin or strong anion exchange resin into a plurality of peptides, comprising trypsin; (d) a transfer buffer for transferring the plurality of peptides in the layer of strong cation exchange resin or strong anion exchange resin into the solid-phase extraction membrane, comprising sodium chloride, ammonium formate or ammonium bicarbonate; and (e) an elution buffer for eluting the plurality of peptides from the solid-phase extraction membrane, comprising (1) ammonium formate or acetic acid, and (2) acetonitrile.

2. The chromatographic separation device of claim 1, wherein the strong cation exchange resin is sulfonic acid-based; and the strong anion exchange resin is a quaternary ammonium group-containing resin.

3. The chromatographic separation device of claim 1, wherein the solid-phase extraction membrane is a C18 membrane.

4. The chromatographic separation device of claim 1, further comprising a reducing solution for reducing the plurality of proteins retained in the layer of strong cation exchange resin or strong anion exchange resin, comprising Tris(2-carboxyethyl)phosphine hydrochloride (TCEP).

5. The chromatographic separation device of claim 1, wherein the transfer buffer comprises 50 mmol/L sodium chloride, 200 mmol/L ammonium formate or 200 mmol/L ammonium bicarbonate.

6. The chromatographic separation device of claim 1, wherein the lysis buffer comprising 10 mmol/L HEPES at pH 7.4, 150 mmol/L NaCl, 600 mmol/L guanidine hydrochloride, and 1% DDM.

7. The chromatographic separation device of claim 1, wherein the elute buffer comprises 5 mmol/L ammonium formate or 0.5% acetic acid.

8. The chromatographic separation device of claim 1, wherein the biological sample is a cell, tissue or body fluid sample.

9. The chromatographic separation device of claim 1, further comprising a dilute solution comprising formic acid.

10. The chromatographic separation device of claim 1, further comprising a device that is automated.

* * * * *